US012685581B2

(12) United States Patent
Tehrani et al.

(10) Patent No.: US 12,685,581 B2
(45) Date of Patent: Jul. 21, 2026

(54) BIPOLAR NEEDLE WITH ADJUSTABLE ELECTRODE FOR GEOMETRICALLY CONTROLLED THERMAL ABLATION OF BIOLOGICAL TISSUE

(71) Applicant: BOSTON SCIENTIFIC SCIMED, INC., Maple Grove, MN (US)

(72) Inventors: Ramin N. Tehrani, Marlborough, MA (US); Christopher A. Benning, Hopkinton, MA (US); George Wilfred Duval, Sudbury, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 786 days.

(21) Appl. No.: 18/071,167

(22) Filed: Nov. 29, 2022

(65) Prior Publication Data

US 2023/0165629 A1 Jun. 1, 2023

Related U.S. Application Data

(60) Provisional application No. 63/283,851, filed on Nov. 29, 2021.

(51) Int. Cl.
*A61B 18/14* (2006.01)
*A61B 18/12* (2006.01)
A61B 18/00 (2006.01)

(52) U.S. Cl.
CPC ...... *A61B 18/1477* (2013.01); *A61B 18/1206* (2013.01); *A61B 2018/00083* (2013.01); *A61B 2018/00577* (2013.01); *A61B 2018/00767* (2013.01); *A61B 2018/00791* (2013.01); *A61B 2018/00875* (2013.01);
(Continued)

(58) Field of Classification Search
CPC ...... A61B 18/1477; A61B 2018/00946; A61B 2018/1425
See application file for complete search history.

(56) References Cited

U.S. PATENT DOCUMENTS

| | | | |
|---|---|---|---|
| 5,019,034 A | 5/1991 | Weaver et al. | |
| 5,370,675 A | 12/1994 | Edwards et al. | |
| 5,403,311 A | 4/1995 | Abele et al. | |

(Continued)

FOREIGN PATENT DOCUMENTS

| | | |
|---|---|---|
| CN | 111529049 A | 8/2020 |
| DE | 19719797 A1 | 10/1997 |

(Continued)

OTHER PUBLICATIONS

Translation of WO-2021068620-A1 (Year: 2021).*

(Continued)

*Primary Examiner* — Sean W Collins
(74) *Attorney, Agent, or Firm* — Seager, Tufte & Wickhem, LLP

(57) ABSTRACT

Methods, apparatuses and systems for ablation therapy. A configurable ablation probe includes at least two electrodes, the surface areas of which can be manipulated and then fixed by the user. Some methods include adjusting the relative surface areas during a sequence of ablation steps to preferentially create lesions closer to one electrode or the other. Some methods include adjusting the position of one of the electrodes during therapy delivery to create elongated lesions.

20 Claims, 10 Drawing Sheets

(52) U.S. Cl.
CPC .................. *A61B 2018/0091* (2013.01); *A61B 2018/00946* (2013.01); *A61B 2018/1425* (2013.01)

(56) References Cited

U.S. PATENT DOCUMENTS

| | | | |
|---|---|---|---|
| 5,599,346 A | 2/1997 | Edwards et al. | |
| 5,718,246 A | 2/1998 | Vona | |
| 5,855,576 A | 1/1999 | Leveen et al. | |
| 5,863,290 A * | 1/1999 | Gough | A61N 1/06 |
| | | | 606/41 |
| 6,010,252 A | 1/2000 | Cipolla | |
| 6,010,613 A | 1/2000 | Walters et al. | |
| 6,041,252 A | 3/2000 | Walker et al. | |
| 6,043,066 A | 3/2000 | Mangano et al. | |
| 6,278,895 B1 | 8/2001 | Bernard | |
| 6,326,177 B1 | 12/2001 | Schoenbach et al. | |
| 6,387,671 B1 | 5/2002 | Rubinsky et al. | |
| 6,428,534 B1 | 8/2002 | Joye et al. | |
| 6,638,277 B2 | 10/2003 | Schaefer et al. | |
| 6,714,816 B1 | 3/2004 | Heller et al. | |
| 6,912,471 B2 | 6/2005 | Heigl et al. | |
| 6,994,706 B2 | 2/2006 | Chornenky et al. | |
| 7,245,963 B2 | 7/2007 | Draghia-Akli et al. | |
| 7,306,595 B2 | 12/2007 | Ostrovsky et al. | |
| 7,306,940 B2 | 12/2007 | Miklavcic et al. | |
| 7,416,549 B2 | 8/2008 | Young et al. | |
| 7,456,012 B2 | 11/2008 | Ryttsn et al. | |
| 7,794,458 B2 | 9/2010 | McIntyre et al. | |
| 7,799,022 B2 | 9/2010 | Fernald et al. | |
| 7,850,681 B2 | 12/2010 | Lafontaine | |
| 8,014,854 B2 | 9/2011 | Schroeppel et al. | |
| 8,048,067 B2 | 11/2011 | Davalos et al. | |
| 8,114,070 B2 | 2/2012 | Rubinsky et al. | |
| 8,152,801 B2 | 4/2012 | Goldberg et al. | |
| 8,211,104 B2 | 7/2012 | McCullagh et al. | |
| 8,251,986 B2 | 8/2012 | Chornenky et al. | |
| 8,282,631 B2 | 10/2012 | Davalos et al. | |
| 8,465,484 B2 | 6/2013 | Davalos et al. | |
| 8,540,710 B2 | 9/2013 | Johnson et al. | |
| 8,603,087 B2 | 12/2013 | Rubinsky et al. | |
| 8,647,338 B2 | 2/2014 | Chornenky et al. | |
| 8,801,709 B2 | 8/2014 | Prakash et al. | |
| 8,915,911 B2 | 12/2014 | Azure | |
| 8,920,416 B2 | 12/2014 | Pham et al. | |
| 8,926,606 B2 | 1/2015 | Davalos et al. | |
| 9,005,189 B2 | 4/2015 | Davalos et al. | |
| 2001/0044596 A1 | 11/2001 | Jaafar | |
| 2002/0058933 A1 | 5/2002 | Christopherson et al. | |
| 2002/0077627 A1 | 6/2002 | Johnson et al. | |
| 2002/0107515 A1 | 8/2002 | Edwards et al. | |
| 2002/0115991 A1 | 8/2002 | Edwards | |
| 2003/0009110 A1 | 1/2003 | Tu et al. | |
| 2004/0015162 A1 * | 1/2004 | McGaffigan | A61B 18/1482 |
| | | | 606/41 |
| 2004/0186468 A1 | 9/2004 | Edwards | |
| 2005/0080409 A1 * | 4/2005 | Young | A61B 18/1492 |
| | | | 606/41 |
| 2005/0267467 A1 | 12/2005 | Paul et al. | |
| 2006/0142801 A1 | 6/2006 | Demarais et al. | |
| 2006/0293730 A1 | 12/2006 | Rubinsky et al. | |
| 2007/0025919 A1 | 2/2007 | Deem et al. | |
| 2008/0009927 A1 | 1/2008 | Vilims | |
| 2008/0275445 A1 | 11/2008 | Kelly et al. | |
| 2009/0247933 A1 | 10/2009 | Maor et al. | |
| 2009/0326638 A1 | 12/2009 | Atanasoska et al. | |
| 2010/0023004 A1 | 1/2010 | Francischelli et al. | |
| 2010/0261994 A1 | 10/2010 | Davalos et al. | |
| 2011/0238057 A1 | 9/2011 | Moss et al. | |
| 2012/0053403 A1 | 3/2012 | Ducharme et al. | |
| 2012/0059309 A1 | 3/2012 | Di Palma et al. | |
| 2012/0150172 A1 * | 6/2012 | Ortiz | A61B 18/1477 |
| | | | 606/41 |
| 2012/0310230 A1 | 12/2012 | Willis | |
| 2012/0330299 A1 | 12/2012 | Webster et al. | |
| 2013/0184702 A1 | 7/2013 | Neal, II et al. | |
| 2013/0281968 A1 | 10/2013 | Davalos et al. | |
| 2014/0121663 A1 | 5/2014 | Pearson et al. | |
| 2014/0128859 A1 | 5/2014 | Lee | |
| 2014/0128936 A1 | 5/2014 | Laufer et al. | |
| 2016/0113707 A1 | 4/2016 | Sahakian et al. | |
| 2016/0113709 A1 | 4/2016 | Maor | |
| 2016/0199661 A1 | 7/2016 | Willard et al. | |
| 2018/0250508 A1 | 9/2018 | Howard | |
| 2019/0223943 A1 * | 7/2019 | Forsyth | A61B 18/1477 |
| 2020/0289185 A1 | 9/2020 | Forsyth et al. | |
| 2020/0289188 A1 | 9/2020 | Forsyth et al. | |
| 2020/0289827 A1 | 9/2020 | Forsyth et al. | |
| 2021/0022860 A1 | 1/2021 | Lally et al. | |
| 2021/0106374 A1 | 4/2021 | Forsyth et al. | |

FOREIGN PATENT DOCUMENTS

| | | | | |
|---|---|---|---|---|
| JP | H1024049 A | 1/1998 | | |
| JP | H10277163 A | 10/1998 | | |
| JP | H11332880 A | 12/1999 | | |
| JP | 2012170777 A | 9/2012 | | |
| JP | 2013536728 A | 9/2013 | | |
| JP | 2021508559 A | 3/2021 | | |
| JP | 2021129981 A | 9/2021 | | |
| WO | WO-2021068620 A1 * | 4/2021 | ........... | A61B 18/148 |

OTHER PUBLICATIONS

Invitation to Pay Additional Fees dated Mar. 29, 2023 for International Application No. PCT/US2022/051226.

StarBurst XL RFA Electrodes, Angiodynamics Inc. 2013. 2 pages.

StarBurst Talon Infusion RFA Electrodes, Angiodynamics Inc. 2013. 2 pages.

Deodhar et al; "Irreversible Electroporation Near the Heart: Ventricular Arrhythmias Can Be Prevented With ECG Synchronization." AJR 196:W330-W335, Mar. 2011. Accessed on Jul. 16, 2019.

Beebe et al; "Nanosecond Pulsed Electric Field (nsPEF) Effects on Cells and Tissues: Apoptosis Induction and Tumor Growth Inhibition", IEEE Transactions on Plasma Science , 6 pages, Mar. 2002.

Kennedy et al; "Cationic Peptide Exposure Enhances Pulsed-Electric-Field-Mediated Membrane Disruption", Plos One, vol. 9, Issue 3, 17 pp. Mar. 2014.

Miklavcic et al; "The Importance of Electric Field Distribution for Effective in Vivo Electroporation of Tissues", Biophysical Journal, vol. 74, pp. 2152-2158, May 1998.

Distelmaier et al; "Midterm Safety and Efficacy of Irreversible Electroporation of Malignant Tumors Located Close to Major Portal or Hepatic Veins", Radiology, vol. 285, No. 3, 1023-1031, Dec. 2017.

Rubinsky et al; "Irreversible Electroporation: A New Ablation Modality—Clinical Implications." Technology in Cancer Research and Treatment, vol. 6, No. 1, pp. 37-48, Feb. 2007.

Swartz et al; "Sparking New Frontiers: Using in Vivo Electroporation for Genetic Manipulations", Developmental Biology, 233, pp. 13-21, 2001.

Tsong, "Electroporation of Cell Membranes," Biophysical Journal, vol. 60, pp. 297-306, Aug. 2, 1991.

International Search Report and Written Opinion dated Apr. 17, 2019 for International Application No. PCT/US2019/014680.

* cited by examiner

BIPOLAR NEEDLE WITH ADJUSTABLE ELECTRODE FOR GEOMETRICALLY CONTROLLED THERMAL ABLATION OF BIOLOGICAL TISSUE

CROSS REFERENCE TO RELATED APPLICATIONS

This application claims the benefit of priority under 35 U.S.C. § 119 of U.S. Provisional Application No 63/283, 851, filed Nov. 29, 2021, the entire disclosure of which is hereby incorporated by reference.

BACKGROUND

Electrical stimuli can be applied to ablate tissue in a variety of forms. Thermal RF ablation and non-thermal irreversible electroporation (IRE) may be used, for example. Even with multiple approaches now available, new and alternative methods for targeted treatment are desired.

SUMMARY

The present inventors have recognized, among other things, that a problem to be solved is the need for new and/or alternative bipolar ablation therapy methods. Such methods may use adjustable electrodes on an ablation probe or catheter.

A first illustrative and non-limiting example takes the form of an ablation probe having a proximal end and a distal end, the probe comprising: an outer sheath of a non-conductive material; an inner sheath of a non-conductive material; a shaft electrode disposed between the inner and outer sheaths; a needle electrode disposed within the inner sheath; a first locking hub configured for selectively locking a relative position of the outer sheath to the shaft electrode; a second locking hub configured for selectively locking a relative position of the shaft electrode to the inner sheath; and a third locking hub configured for selectively locking a relative position of the inner sheath to the needle electrode.

Additionally or alternatively, the needle electrode, inner sheath, shaft electrode, and outer sheath are each moveable relative to one another when none of the locking hubs are locked. Additionally or alternatively, the needle electrode includes a tissue piercing distal tip. Additionally or alternatively, the third locking hub facilitates a step of defining an exposed surface area of the needle electrode, and the first locking hub facilitates a step of defining an exposed surface area of the shaft electrode, such that, in use, a user may lock the first and third locking hubs while moving the needle electrode, having a fixed surface area, relative to the shaft electrode, also having a fixed surface area. Additionally or alternatively, the ablation probe may comprise means to indicate electrically a change in exposed surface area of at least one of the shaft and needle electrodes. Additionally or alternatively, the ablation probe may comprise means to indicate electrically a change in the distance between the shaft and needle electrodes. Additionally or alternatively, the needle electrode comprises a lumen therethrough to allow a fluid to be infused. Additionally or alternatively, the outer sheath includes a lumen therethrough allowing a fluid to be infused.

Additionally or alternatively, the ablation probe may be included in system for ablation also comprising a signal generator adapted for electrical connection to each of the needle electrode and the shaft electrode, the signal generator configured to sense an impedance between the needle electrode and the shaft electrode during therapy delivery to maintain a therapy current as the needle electrode and the shaft electrode are moved relative to one another. The therapy current may be a constant current. Additionally or alternatively, the system or probe may include a temperature sensor associated with at least one of the shaft electrode or the needle electrode. Additionally or alternatively, the ablation probe may be included in system for ablation also comprising a signal generator adapted for electrical connection to each of the needle electrode and the shaft electrode, the signal generator configured to sense an impedance between the needle electrode and the shaft electrode during therapy delivery and to obtain a temperature signal from the temperature sensor, and to adjust a therapy voltage responsive to the temperature and impedance signals.

Additionally or alternatively, the signal generator is configured to operate as follows: at initiation of a therapy output, sensing temperature and impedance; maintain or increase voltage until the sensed temperature reaches a temperature threshold; measure impedance and voltage once the sensed temperature reaches the temperature threshold and store a target current; after the temperature threshold is reached, monitor impedance to maintain the target current; and if the sensed temperature rises above the temperature threshold, reduce the target current.

Additionally or alternatively, the signal generator is configured to sense a distance between the electrodes and a surface area of the electrodes by linking to the locking hubs. Additionally or alternatively, the signal generator is configured to adjust the sensed impedance to account for the distance between the electrodes and/or the surface area of the electrodes. Additionally or alternatively, the signal generator is configured to provide ablation signals for irreversible electroporation and thermal ablation.

Another illustrative and non-limiting example takes the form of method of ablating a tissue region using a therapy probe having a shaft with proximal and distal ends, and a plurality of therapy delivery electrodes at the distal end thereof, the method comprising: inserting the therapy probe to place the distal end of the shaft at a desired location, the distal end of the shaft including a shaft electrode having an exposed portion proximal of the distal end of the shaft, a surface area of the exposed portion of the shaft electrode being adjustable; advancing a needle electrode from the shaft to a desired position and manipulating a needle electrode sheath that adjustably exposes a portion of the needle electrode to thereby control a surface area of the exposed portion of the needle electrode; delivering a first therapy while a surface area of the exposed portion of the needle electrode exceeds a surface area of the exposed portion of the shaft electrode, to thereby develop a first lesion adjacent the shaft electrode; and delivering a second therapy while a surface area of the exposed portion of the shaft electrode exceeds the surface area of the exposed portion of the needle electrode, to thereby develop a second lesion adjacent the needle electrode.

Additionally or alternatively, the method may further comprise manipulating the exposed portion of the needle electrode between the steps of delivering the first therapy and delivering the second therapy. Additionally or alternatively, the method may further comprise manipulating the exposed portion of the shaft electrode between the steps of delivering the first therapy and delivering the second therapy.

Additionally or alternatively, the therapy probe is configured such that the position of the exposed portion of the shaft electrode is adjustable relative to the distal end of the therapy probe, and the method further comprises adjusting the position of the exposed portion of the shaft electrode between the steps of delivering the first therapy and delivering the second therapy. Additionally or alternatively, the first therapy takes the form of a thermal RF ablation therapy, and the second therapy takes the form of a thermal RF ablation therapy.

Additionally or alternatively, the therapy probe comprises: an outer sheath of a non-conductive material; the needle electrode sheath, also of a non-conductive material; the shaft electrode disposed between the needle electrode sheath and the outer sheath; the needle electrode disposed within the needle electrode sheath; a first locking hub configured for selectively locking a relative position of the outer sheath to the shaft electrode; a second locking hub configured for selectively locking a relative position of the shaft electrode to the needle electrode sheath; and a third locking hub configured for selectively locking a relative position of the needle electrode sheath to the needle electrode.

Additionally or alternatively, the method may further comprise locking the first and third locking hubs before delivering the first therapy; unlocking at least one of the first or third locking hubs after delivering the first therapy and manipulating the exposed surface area of at least one of the shaft electrode or the needle electrode; relocking the at least one of the first or third locking hubs after manipulating the exposed surface area of the at least one of the shaft electrode or he needle electrode, before delivering the second therapy.

Another illustrative, non-limiting example takes the form of a method of ablating a tissue region using an ablation probe having a shaft with proximal and distal ends, and a plurality of therapy delivery electrodes at the distal end thereof, the method comprising: inserting the ablation probe to place the distal end of the shaft at a desired location, the distal end of the shaft including a shaft electrode having an exposed portion proximal of the distal end of the shaft, a surface area of the exposed portion of the shaft electrode being adjustable; advancing a needle electrode from the shaft to a desired position and manipulating a needle electrode sheath that adjustably exposes a portion of the needle electrode to thereby control a surface area of the exposed portion of the needle electrode; delivering a first therapy while a surface area of the exposed portion of the shaft electrode exceeds the surface area of the exposed portion of the needle electrode, to thereby develop a first lesion adjacent the needle electrode and, during delivery of the first therapy, withdrawing the needle electrode from the desired position and into the shaft while maintaining the exposed surface area of the needle electrode, to thereby extend the first lesion in a longitudinal direction relative to an axis of the needle electrode.

Additionally or alternatively, the therapy probe comprises: an outer sheath of a non-conductive material; the needle electrode sheath, also of a non-conductive material; the shaft electrode disposed between the needle electrode sheath and the outer sheath; the needle electrode disposed within the needle electrode sheath; a first locking hub configured for selectively locking a relative position of the outer sheath to the shaft electrode; a second locking hub configured for selectively locking a relative position of the shaft electrode to the needle electrode sheath; and a third locking hub configured for selectively locking a relative position of the needle electrode sheath to the needle electrode.

Additionally or alternatively, the method may further comprise locking the first and third locking hubs before delivering the first therapy, to thereby fix the exposed surface areas of each of the shaft electrode and the needle electrode, while leaving the second locking hub unlocked to allow withdrawal of the needle electrode from the desired position and into the shaft.

Additionally or alternatively, the method may further comprise reducing a power level of the first therapy as the needle electrode is withdrawn from the desired position and into the shaft. Additionally or alternatively, the method may further comprise sensing an impedance between the needle electrode and the shaft electrode, and sensing at least one temperature at a position adjacent the needle electrode, and responsive to the sensed impedance and at least one temperature, adjusting the power level of the first therapy as the needle electrode is withdrawn from the desired position and into the shaft.

Another illustrative and non-limiting example takes the form of a method of ablating a tissue region using an ablation probe having a shaft with proximal and distal ends, and a plurality of therapy delivery electrodes at the distal end thereof, the method comprising: inserting the ablation probe to place the distal end of the shaft at a desired location, the distal end of the shaft including a shaft electrode having an exposed portion proximal of the distal end of the shaft, a surface area of the exposed portion of the shaft electrode being adjustable; advancing a needle electrode from the shaft to a desired position and manipulating a needle electrode sheath that adjustably exposes a portion of the needle electrode to thereby control a surface area of the exposed portion of the needle electrode; delivering a first therapy while a surface area of the exposed portion of the shaft electrode exceeds the surface area of the exposed portion of the needle electrode, to thereby develop a first lesion adjacent the needle electrode and, during delivery of the first therapy, advancing the needle electrode from the desired position out of the shaft while maintaining the exposed surface area of the needle electrode, to thereby extend the first lesion in a longitudinal direction relative to an axis of the needle electrode.

Additionally or alternatively, the therapy probe comprises: an outer sheath of a non-conductive material; the needle electrode sheath, also of a non-conductive material; the shaft electrode disposed between the needle electrode sheath and the outer sheath; the needle electrode disposed within the needle electrode sheath; a first locking hub configured for selectively locking a relative position of the outer sheath to the shaft electrode; a second locking hub configured for selectively locking a relative position of the shaft electrode to the needle electrode sheath; and a third locking hub configured for selectively locking a relative position of the needle electrode sheath to the needle electrode.

Additionally or alternatively, the method may further comprise locking the first and third locking hubs before delivering the first therapy, to thereby fix the exposed surface areas of each of the shaft electrode and the needle electrode, while leaving the second locking hub unlocked to allow advancement of the needle electrode during the first therapy.

Additionally or alternatively, the locking hubs are provided on an assembly comprising visible indicia indicating how much of the needle electrode is exposed, and the method comprises using the visible indicia to determine how much of the needle electrode is exposed. Additionally or alternatively, the locking hubs are provided on an assembly comprising visible indicia indicating how much of the shaft electrode is exposed, and the method comprises using the visible indicia to determine how much of the shaft electrode is exposed. Additionally or alternatively, the method may further comprise increasing a power level of the first therapy as the needle electrode is advanced. Additionally or alternatively, the first therapy is an RF ablation therapy.

Additionally or alternatively, the method may further comprise sensing an impedance between the needle electrode and the shaft electrode, and sensing at least one temperature at a position adjacent the needle electrode, and responsive to the sensed impedance and at least one temperature, adjusting the power level of the first therapy as the needle electrode is advanced.

This overview is intended to provide an introduction to the subject matter of the present patent application. It is not intended to provide an exclusive or exhaustive explanation. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
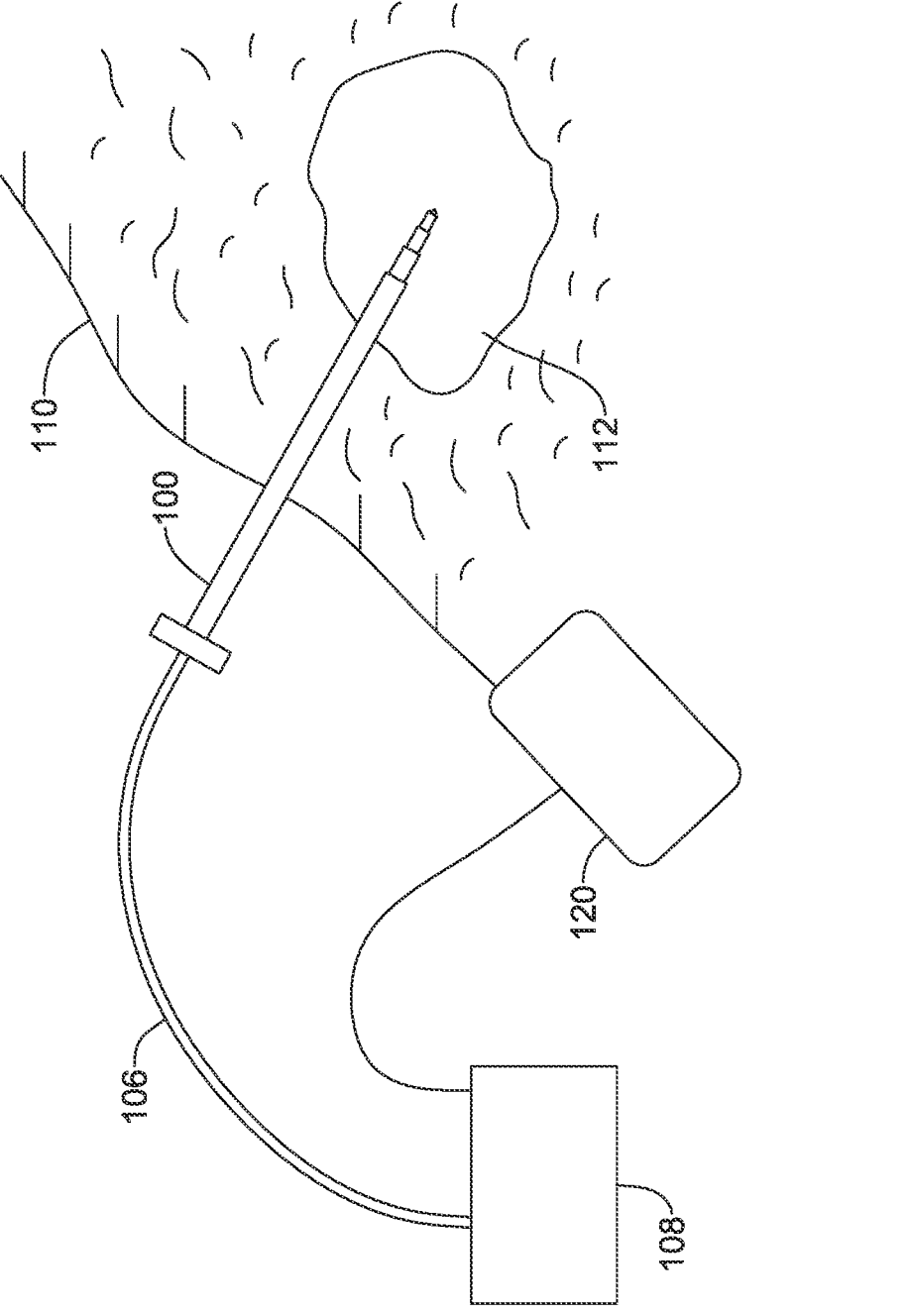
FIG. 1 shows an illustrative ablation system.

FIG. 1 shows an illustrative ablation system. The system includes an ablation probe 100 that is adapted for insertion into tissue of a patient 110 to access a target region 112, which may be, for example, an organ, diseased tissue, a tumor, etc. At the distal end (the end that is inserted to the patient) is a tissue piercing electrode 102. A plurality of tissue piercing electrodes may be used instead of the single electrode 102 that is shown. For example, a plurality of tissue piercing electrodes taking the form of an array may use designs as shown in US PG Pub. No. 2019/0223943, and/or U.S. Pat. Nos. 5,855,576 and 6,638,277, the disclosures of which are incorporated herein by reference to show ablation probe designs and describe various features and methods of their use. The tissue piercing electrode 102 may be advanced and retracted relative to the distal end of the ablation probe 100. More details regarding the distal portion of the illustrative ablation probe 100 are described below.

The ablation probe 100 is coupled by a wire 106 to a signal generator 108. The signal generator may include, for example and without limitation, control circuitry, including digital and/or analog circuits for shaping/defining output waveforms, which can be square waves, sinusoidal waves, or any other suitable output. The signal generator may be battery powered, but, in most instances, will draw line power such as by plugging into a wall outlet. The signal generator 108 may include circuitry therein for measuring output impedance of signals delivered via the probe 100. For example, a microcontroller or microprocessor may be provided, as well as sample/hold circuitry, measurement circuitry, comparators, filtering circuitry, operational amplifiers, etc. for receiving and measuring signals. Output circuitry may include, for example and without limitation, an output H-Bridge for high power outputs, or using other architectures, as well as any other suitable switching or resonant circuitry, as desired. Output circuitry may include, for example, IGBT transistors for higher power systems; other electronic componentry may be used with known tradeoffs between speed, rise time, current capacity, cost, size, etc. The signal generator 108 may also be configured to couple to one or more temperature sensors, such as thermistors or other temperature sensing devices located in or on the ablation probe 100, to obtain or receive signals therefrom and interpret received data, allowing temperature at select locations to be measured and/or monitored. For example, with thermal ablation, a target temperature range (such as 50-100° C., 55-80° C., 60-70° C., etc.) may be defined for issuing therapy outputs that will cause a desired amount of cell death without undue side effects or hazards. The target temperature may be maintained for a desired period of time (such as 10 to 60 seconds, or 20-30 seconds, as desired). With non-thermal ablation, such as IRE, a temperature sensor may be used to ensure that tissue temperature is staying within a relatively lower range (such as <50° C., <42° C., etc.). Some examples of ablation generators may be found in US PG Pat. Pub. Nos. 20210228260, 20210106374, 20200289827, 20200289188, and/or 20200289185, the disclosures of which are incorporated herein by reference, though the signal generator 108 may take other forms.

As used herein, a monopolar therapy is one in which a return electrode, such as patch electrode 120, is placed on the patient 110, such as on the patient's skin, such that electric current passes through the tissue between an electrode on or extended from the ablation probe 100 and the return electrode 120, as determined by electrical fields generated therebetween. A bipolar therapy is one in which two electrodes both inserted in relative proximity to one another pass current therebetween, such as between the electrode 102 and an electrode on the ablation probe 100 (see FIGS. 2-4). While a patch electrode 120 may still be applied as an indifferent or grounding electrode, almost all current in a bipolar therapy passes between the inserted electrodes.

Figure 2:
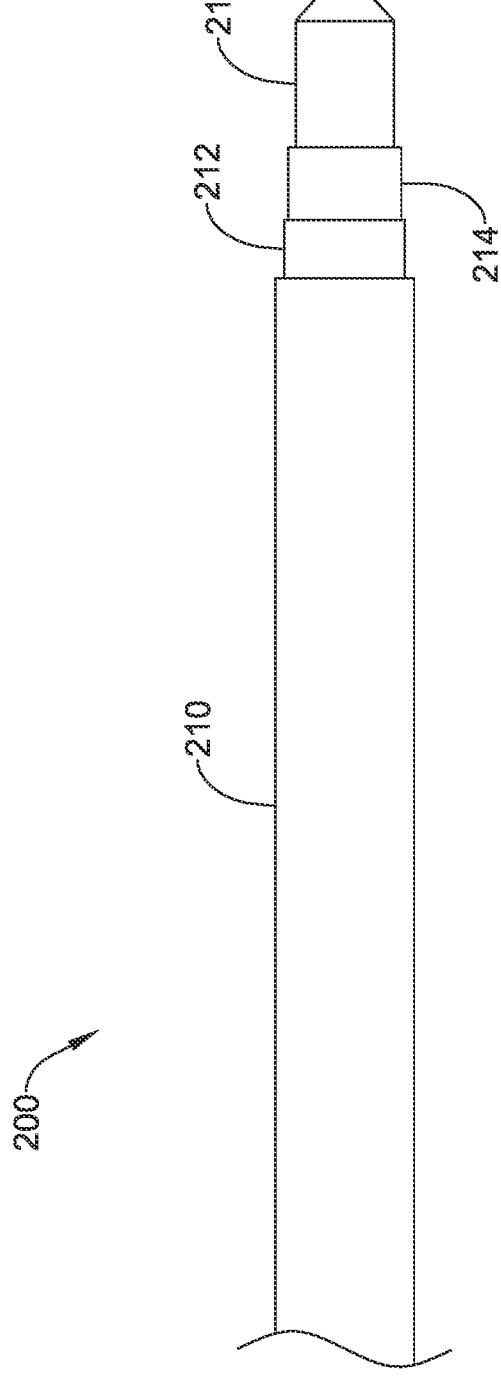
FIGS. 2-4 illustrate aspects of a distal end of an ablation probe.
Figure 3:
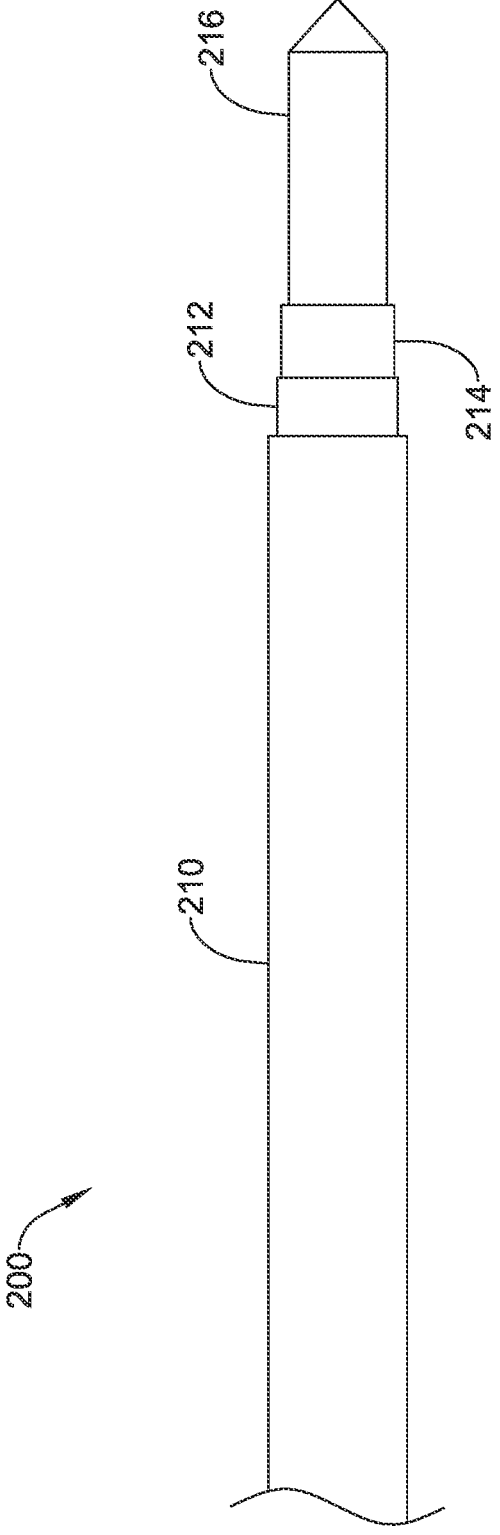
Figure 4:
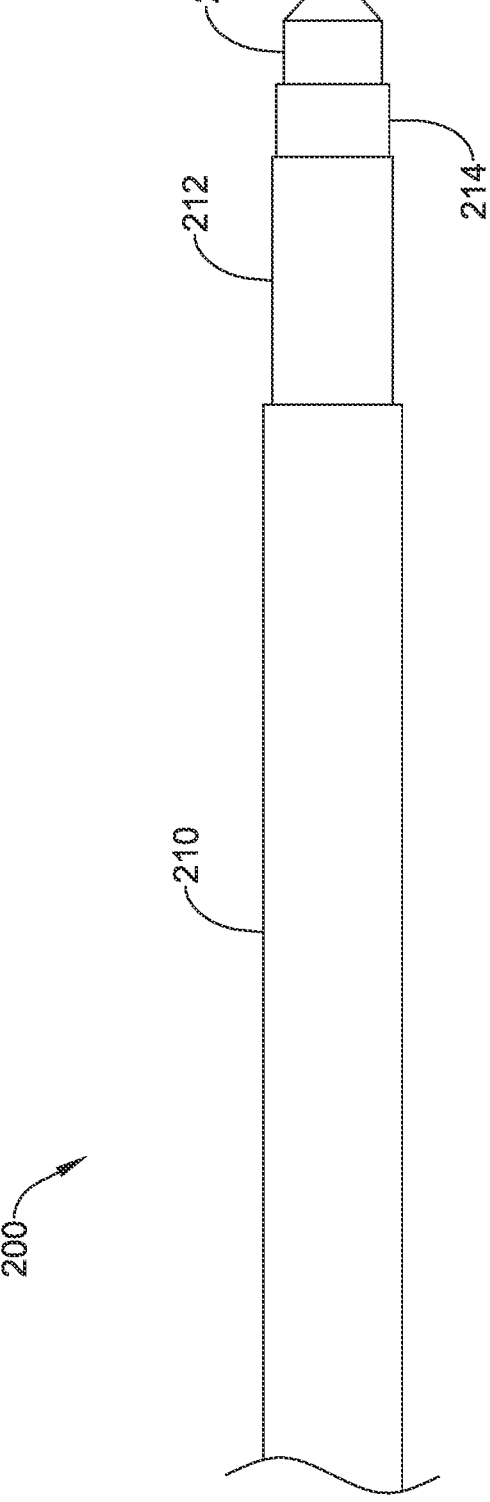

FIGS. 2-4 illustrate aspects of a distal end of an ablation probe. A particular probe distal end structure is shown at 100. An outer sheath 210 is provided over a shaft electrode 212, which resides over an inner sheath 214. A needle electrode 216 sits within the inner sheath. The outer sheath 210 and inner sheath 214 may be made of any suitable medical grade insulative material. Examples may include, without limitation, polyimide, poly-ether block amides, and other insulative polymers. The shaft electrode 212 and needle electrode 216 may be made of any suitable material, including, for example and without limitation, stainless steel, gold, titanium, and other conductive metals, as well as, optionally conductive polymers, as desired.

The outer sheath 210 may take the form of a hollow tube having one or more lumens therein; the outer sheath 210 may have a plurality of longitudinal segments attached together, if desired. The shaft electrode 212 is moveable relative to the outer sheath 210 as well as the inner sheath 214. The shaft electrode 212 itself may also be a tubular element having a lumen therethrough, such as a cylindrical electrode or a hypotube. In some examples, the shaft electrode 212 includes a first section including that part shown with a tubular distal portion, and a second, more proximal part taking the form of an elongated, conductive push/pull wire, which may reduce the friction associated with movement of the shaft electrode 212.

The inner sheath may also be a hollow tubular element, and may extend as a tube its entire length or, as with the shaft electrode 212, may comprise a tubular, insulative distal portion coupled to a push/pull member such as an elongated (and, as desired, insulated) wire. The needle electrode 216 may have a sharpened or pointed distal tip, as shown in FIG. 2, or may be blunted if desired for example if used within a body lumen such as a blood vessel or in the biliary tree. The needle electrode 216 may take the form of a single hypotube, with a tip cap having the end tip, or may be a crimped or otherwise collapsed hypotube. In some examples, a single elongated hypotube is used for the needle electrode. In other examples, the needle electrode may be an assembly including a push wire coupled to a distal tip portion.

Though not shown, the outer sheath 210 may also include a lumen for fluid infusion, either out the distal end of the sheath 210, or though the inner sheath 214, or through one or more side openings (not shown). Fluid may be infused, for example, in tissue that is relatively lacking in water content (such as the prostate) to aid in ionic flow during therapy delivery, to reduce local impedance, or to inject dye, drugs or biologic substances in the target region. The outer sheath 210 and/or the inner sheath 214 may include one or more fluid passing lumens for aspirating fluid before, during or after a procedure, if desired. The needle electrode 216 may also include a lumen therethrough to allow fluid to be infused.

In various examples, the pieces shown (outer sheath 210, shaft electrode 212, inner sheath 214, and needle electrode 216 can be advanced and retracted relative to one another. Thus, for example and without limitation, in use, each of the shaft electrode 212, inner sheath 214, and needle electrode 216 may be advanced to a target region while retracted within the outer sheath 210, and then individually or in unison (or in stages) advanced therefrom. Once so placed, any of the needle electrode 216, the inner sheath 214, and the shaft electrode 212, may be advanced or retracted relative to the outer sheath 210, as desired and without requiring other parts to move. Moreover, the outer sheath 210 may be advanced over the other elements as desired. As a result, the exposed surface area of the shaft electrode 212 can be controlled or manipulated by advancing and retracting the outer sheath 210 in relation to the shaft electrode 212 and/or by advancing or retracting the shaft electrode relative to the outer sheath. Likewise, the exposed surface area of the needle electrode 216 can be controlled or manipulated by advancing and retracting the inner sheath 214 in relation to the needle electrode 216 and/or by advancing or retracting the needle electrode relative to the inner sheath 214. Finally, the distance between the exposed region of the needle electrode 216 and the shaft electrode 212 may also be manipulated by advancing or retracting the needle electrode 216 relative to the shaft electrode 212 and/or by advancing or retracting the shaft electrode 212 relative to the needle electrode 216.

In addition, in some examples, elements may be selectively locked together for the movements just described. In an example, the outer sheath 210 is locked into a position using a proximal locking apparatus (FIGS. 8-9, below) relative to the shaft electrode 212, and/or the inner sheath 214 is locked into a position using a proximal locking apparatus (FIGS. 8-9, below) relative to the needle electrode, thereby fixing the exposed region of each electrode while still allowing relative movement therebetween.

The manipulation of electrode size and spacing is illustrated by reference to FIGS. 2-4. In FIG. 2, a first relative positioning and spacing is shown. FIG. 3 illustrates advancement of the needle electrode 216 relative to the inner sheath 214 as well as the outer sheath 210 and shaft electrode 212, exposing more of the surface area of the needle electrode 216 and advancing the needle electrode 216 into tissue. In FIG. 4, as compared to FIG. 2, each of the needle electrode 216, inner sheath 214, and shaft electrode 212 have been advanced relative to the outer sheath 210. Comparing FIG. 4 to FIG. 3, it can be seen that the needle electrode and outer shaft may be similarly juxtaposed in the two figures, but the inner sheath 214 and the shaft electrode 212 are both advanced relative to the needle electrode 216 and the outer sheath 210.

In some examples, the ablation generator may be configured to control therapy to account for impedance and temperature. Using, for example, a microcontroller and monitoring voltage across a pair of therapy issuing electrode and current passing between the electrodes, the impedance of tissue can be measured. A temperature sensor, as noted above, may be used to capture temperature. During use, the ablation generator can thus be configured to both sense an impedance between the needle electrode and the shaft electrode during therapy delivery and to obtain a temperature signal from the temperature sensor, and to adjust a therapy voltage responsive to the temperature and impedance signals. In a use example, at initiation of a therapy output, the signal generator senses temperature and impedance, and maintains or increases voltage until the sensed temperature reaches a temperature threshold. Alternatively, pulse width or pulse repetition rate, or duty cycle, may be increased, separately or along with voltage, until the sensed temperature reaches the temperature threshold. The signal generator can be configured to continue to measure impedance and voltage once the sensed temperature reaches the temperature threshold and stores a target current. The signal generator can then, after the temperature threshold is reached, monitor impedance to maintain the target current. If the sensed temperature rises above the temperature threshold, the signal generator can then reduce the target current. Such operations by the signal generator can be performed to maintain selected ablation conditions while the electrode surface areas and/or position are manipulated.

Figure 5:
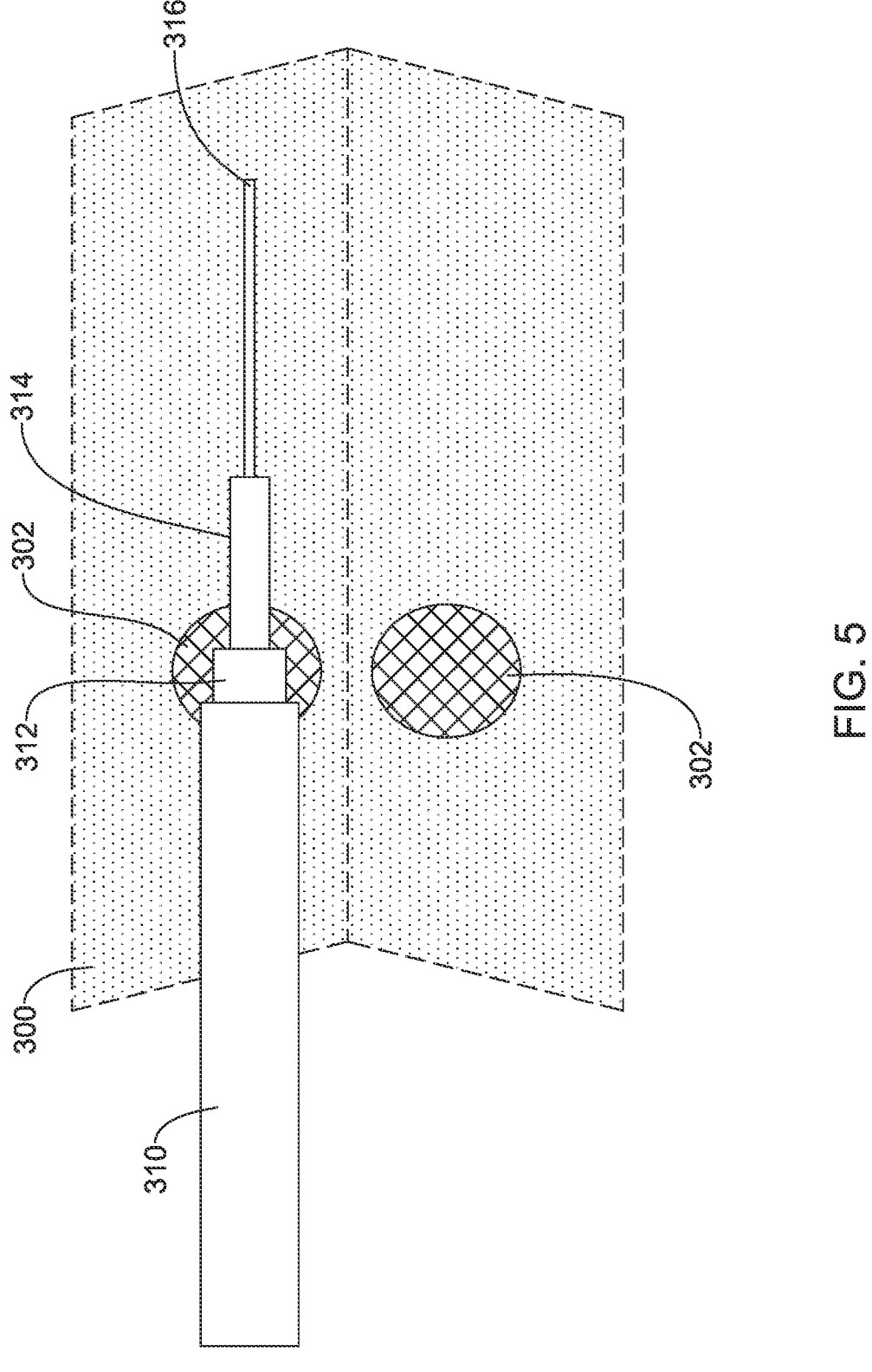
FIGS. 5-7 show illustrative ablation steps.
Figure 6:
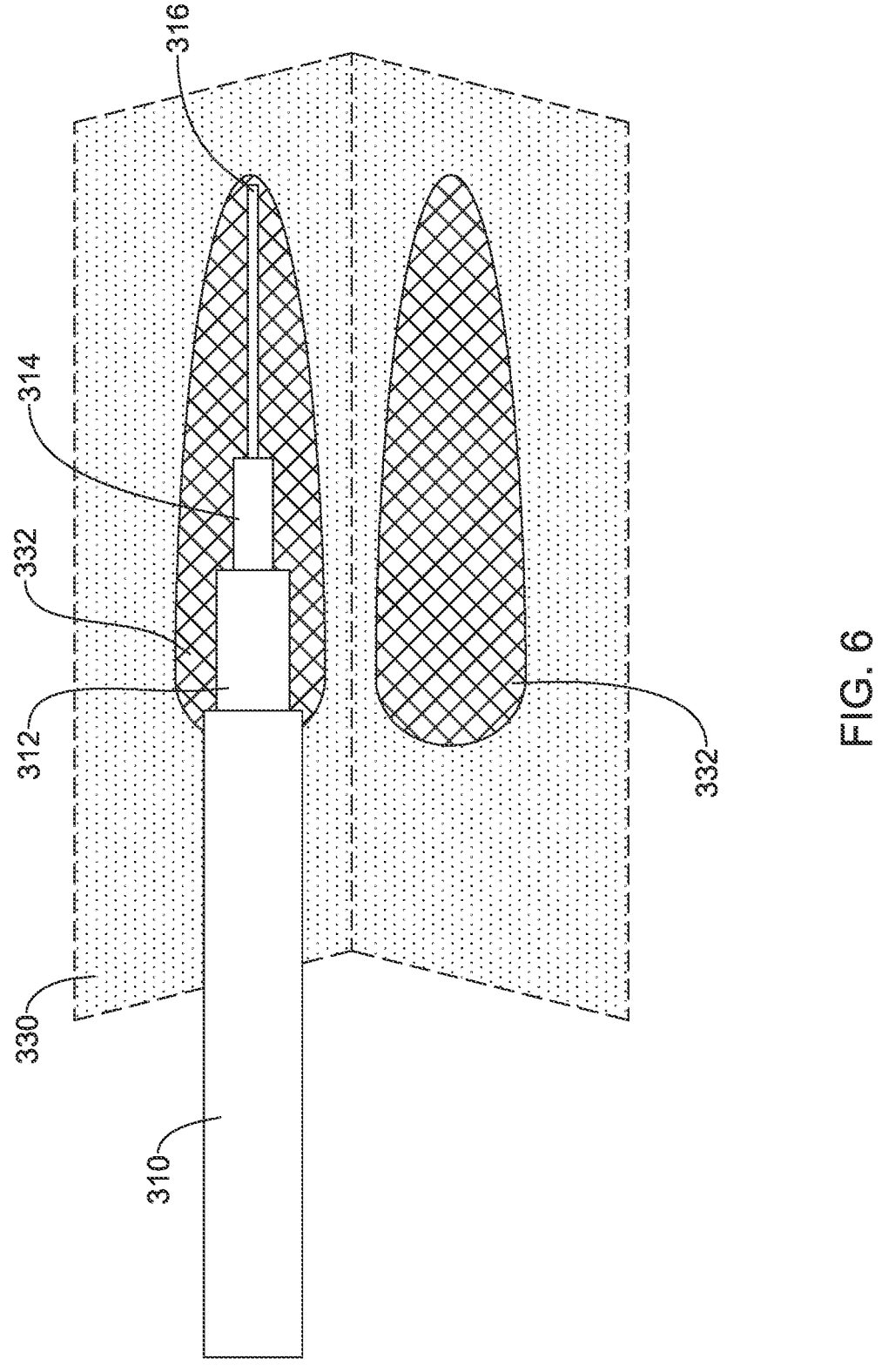
Figure 7:
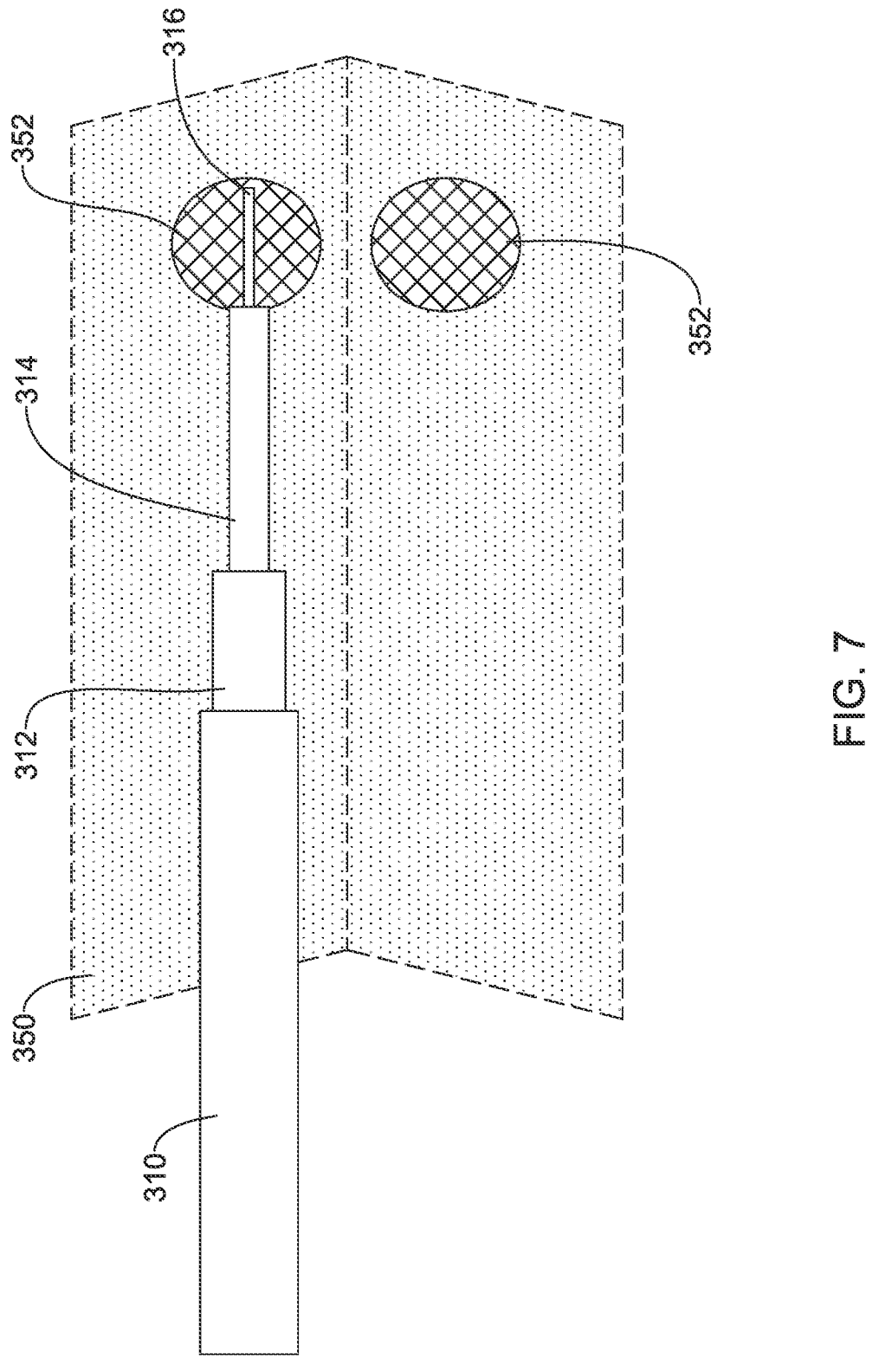

In some examples, the reconfiguration or manipulation of electrode surface areas and/or positioning can be performed as part of a therapy regimen. During delivery of a bipolar therapy, including for a thermal ablation therapy, the locus of thermal ablation will tend to be closest to whichever of the therapy output electrode poles has a lesser surface area. This is because the current density near the smaller electrode will be higher, and higher current density yields higher temperatures. As a result, manipulating the exposed surface area of the electrodes between thermal ablation steps can be used to focus the ablation therapy to specific locations. FIGS. 5-7 show illustrative ablation steps highlighting this capability.

FIGS. 5-7 illustrate steps of ablation procedures and show resultant lesions. In these drawings, tissue samples 300, 330, 350 are shown cut open following delivery of an ablation therapy using an ablation probe. The drawing is based on a test performed using liver tissue. The ablation probe is similar to that shown in FIGS. 2-4, with an outer sheath 310, a shaft electrode 312, an inner sheath 314, and a needle electrode 316, each moveable relative to one another as described above. In FIG. 5, before delivering an ablation output, parts of the ablation probe are manipulated so that the exposed surface area of the shaft electrode 312 is less than the exposed surface area of the needle electrode 316. When RF ablation therapy is enabled, the resultant lesion 302 will occur near and adjacent to the shaft electrode 312, because the current density in this volume of tissue is greatest. Higher current density results in greater localized heating. In FIG. 6, before delivering an ablation output, parts of the ablation probe are manipulated so that the exposed surface area of the shaft electrode 312 is approximately the same as the exposed surface area of the needle electrode 316. The resulting lesion 332 is more elongated, as the current density will be more consistent within a volume between the electrodes. In FIG. 7, before delivering an ablation output, parts of the ablation probe are manipulated so that the exposed surface area of the shaft electrode 312 is greater than the exposed surface area of the needle electrode 316. The resulting lesion 352 is adjacent the needle electrode 316. Again, the location of the lesion 352 is a result of the increased current density near the smaller surface area electrode, which in this case is the needle electrode 316.

The phrase, "approximately the same," used to describe FIG. 6, can mean within +/-10%, or +/-5%, or +/-2%, or +/-1%, in some examples. This may be contrasted with less than or greater than, as used in the examples of FIGS. 5 and 7, which means a difference of greater than 10%, or greater than 20%, or greater than 33%, or greater than 50%. It should be noted that to achieve the lesion of FIG. 6, as opposed to those of FIGS. 5 and 7, the output amplitude or pulse width may be higher, or the therapy may be output for a greater period of time, to bring the larger volume of tissue up to the needed temperature (such as 50-100° C., 55-80° C., 60-70° C., etc.).

Some examples may include performing an ablation step as shown by FIG. 6, then manipulating the ablation probe 310 by moving one or more of the outer sheath 310, shaft electrode 312, inner sheath 314, and/or needle electrode 316 to adjust the relative surface areas of the needle electrode 316 and shaft electrode 312. For example, the elongated lesion of FIG. 6 may be formed, followed by making more localized lesions adjacent each electrode 312, 316 using the configurations of FIG. 5 and then FIG. 7. In another example, the localized lesions of FIGS. 5 and 7 are made first, followed by the elongated lesion of FIG. 6. In still other examples, the lesion shown in FIG. 6 may be formed first, and then the lesion of FIG. 7, or the lesion of FIG. 7 formed first, followed by the lesion of FIG. 6. Any such ordering or reordering may be performed as needed.

In still other examples, the different lesions formed may be formed using different modalities. For example, a lesion as shown in FIG. 6 may be formed first using IRE-type waveforms of shorter pulse width and higher amplitude, followed by forming the lesions of FIGS. 5 and/or 7 using RF ablation waveforms of longer pulse width and lesser amplitude. The differences between IRE and RF are not insignificant; IRE may use pulse widths that are 1 to 3 orders of magnitude less than those of RF, and the amplitude for IRE may be 2 to 4 times that of RF, for example.

As an example, when considering in vivo electroporation of liver tissue, the reversible electroporation threshold field strength may be about 360 V/cm, and the irreversible electroporation threshold field strength may be about 680 V/cm, as described in U.S. Pat. No. 8,048,067. The field for electroporation has typically been applied by delivering a series of individual pulses each having a duration in the range of tens to hundreds of microseconds. For example, U.S. Pat. No. 8,048,067 describes a series of eight 100 microsecond pulses delivered at 1 second intervals. The '067 patent describes analysis and experiments performed to illustrate that the area between lines 20 and 30 in FIG. 1 actually exists, and that a non-thermal IRE method can be achieved.

The tissue membrane does not return instantaneously, from a porated state. As a result, the application of pulses close together in time can have a cumulative effect as described, for example, in U.S. Pat. No. 8,926,606. In addition, a series of pulses can be used to first porate a cell membrane and then move large molecules through generated, reversible pores, as described in US PG Patent App. Pub No. 2007/0025919.

While U.S. Pat. No. 8,048,067 discusses performing IRE without thermal effects, and U.S. Pat. No. 8,926,606 discusses achieving IRE using cumulative effects of closely spaced pulses, the present invention in some examples is directed at combination therapy. For example, a single device using either one output circuit having programmable or reconfigurable features, or a single device having a plurality of output circuits tuned to different regions (in terms of voltage, pulse width, or other parameters), may be used to purposefully deliver both thermal and non-thermal ablation therapies.

In an example, an IRE field in a series of pulses (such as, for example, 8 pulses of 100 microsecond duration at 800 volts per centimeter delivered at about 1 Hz) is issued as one therapy that either precedes or follows thermal ablation output (for example, 8 pulses of 10 millisecond duration at 300 volts per centimeter delivered at about 10 Hz). Other pairings and sequences may be used.

IRE may be delivered as a series of 1 to 1000 pulses with durations in the 0.1 to 100 microsecond range (or more) at a frequency of 1 to 100 Hz (or more or less), for example, 8 to 10 pulses of 5 microsecond duration at 10 Hz may be delivered. The voltage selected for IRE may be above the IRE threshold (as noted above, for liver tissue, the IRE threshold may be in the range of 680 V/cm), though with closely spaced pulses the voltage used may be lower if desired, assuming a cumulative effect can be had. Thermal ablation, on the other hand, may use a relatively longer pulse width (100 microseconds or more, typically 1 millisecond or more), and any voltage suitable to the particular application. Thermal ablation may use, for example, a relatively lower voltage but longer pulse width and/or higher duty cycle than IRE. Voltages may be, for example and without limitation, in the range of 100 to 500 V/cm, or lower or higher if desired. As used herein, duty cycle refers to the ratio of "on time" (active output) to off time (zero output) for a given therapy while the therapy is ongoing. Duty cycle may be referenced from the first pulse of a programmed therapy output to the last pulse of the programmed therapy output, for example, encompassing bursts of therapy outputs and the downtime between bursts.

For purposes of this illustration, the "IRE" therapy steps may have thermal effects as well, but predominantly use IRE to cause cell death; likewise, the predominant mode of cell death for the "Thermal" therapy steps will be thermal though IRE may occur in some cells as well. Factors that may differentiate Thermal from IRE therapy may include duty cycle and field strength or amplitude. Determination of whether thermal or IRE therapy has been effective can be determined through staining using immune-histo-chemical assays, which will illustrate differentiation between tissue regions subject to different types of cell death. For example, immunological response to IRE-caused cell death is distinguishable from that for thermally destroyed cells; cells that survive and/or are only subject to reversible electroporation will further show a demarcation.

In some examples a monopolar therapy mode is used for thermal ablation using a lower voltage gradient, and a bipolar therapy mode is used for IRE using a higher voltage gradient. IRE therapy may use monophasic or biphasic (or triphasic or other multiphasic) electrical output, generated with relatively high amplitudes (yielding fields of over 600 V/cm, for example) and short pulsewidths (for example in the range of 0.1 to 100 microseconds) at a relatively lower duty cycle (such as repetition rate of 1 to 100 Hz and thus a duty cycle of less than 0.1%), which may avoid thermal heating to yield predominantly IRE therapy. The therapy may include injection of a fluid to enhance or modify effectiveness or spatial effects of an applied electrical therapy, or may instead be injection of an ablative fluid such as a fluid having limited caustic effects, or cooling or heating effects.

Thermal ablation may incorporate somewhat lower pulse amplitudes (fields of less than 600 V/cm, for example) at longer pulsewidths (for example, 10 microseconds to 100 milliseconds) at a relatively higher duty cycle (such as by application of the pulses at a frequency of 10 Hz to 100 kHz, in some examples to yield a duty cycle of greater than 0.1%). For example, saline may be injected to reduce local tissue impedance, increasing current flow for a given output voltage, such that both an electrical output is delivered and the fluid. While various numerical examples are given here, the present invention may be implemented using the ranges disclosed for IRE or thermal ablation, as well as other ranges unless otherwise specifically recited in a corresponding claim.

Figure 8:
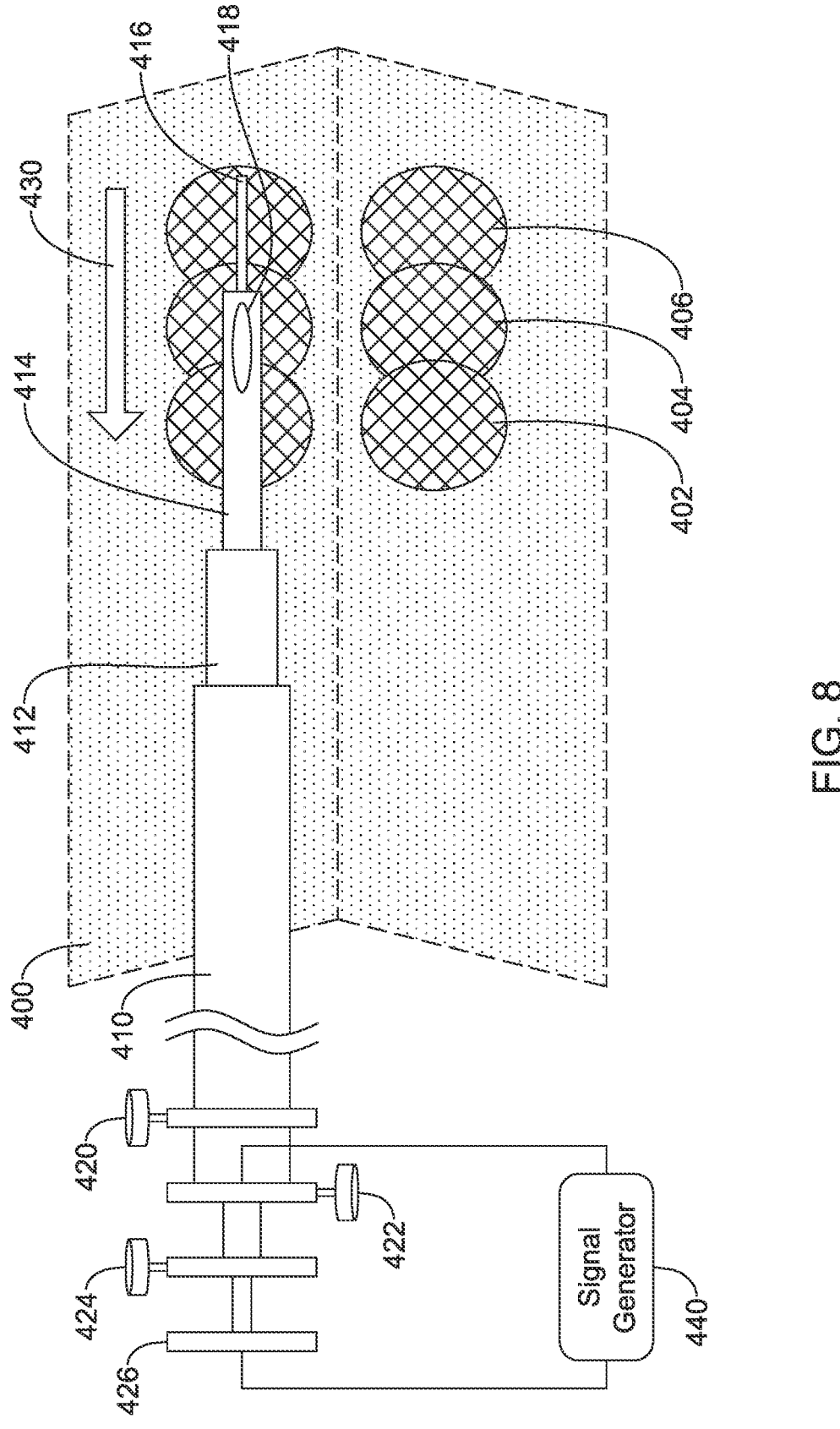
FIGS. 8-9 show additional ablation procedure steps with additional detail on the proximal end of an ablation probe.
Figure 9:
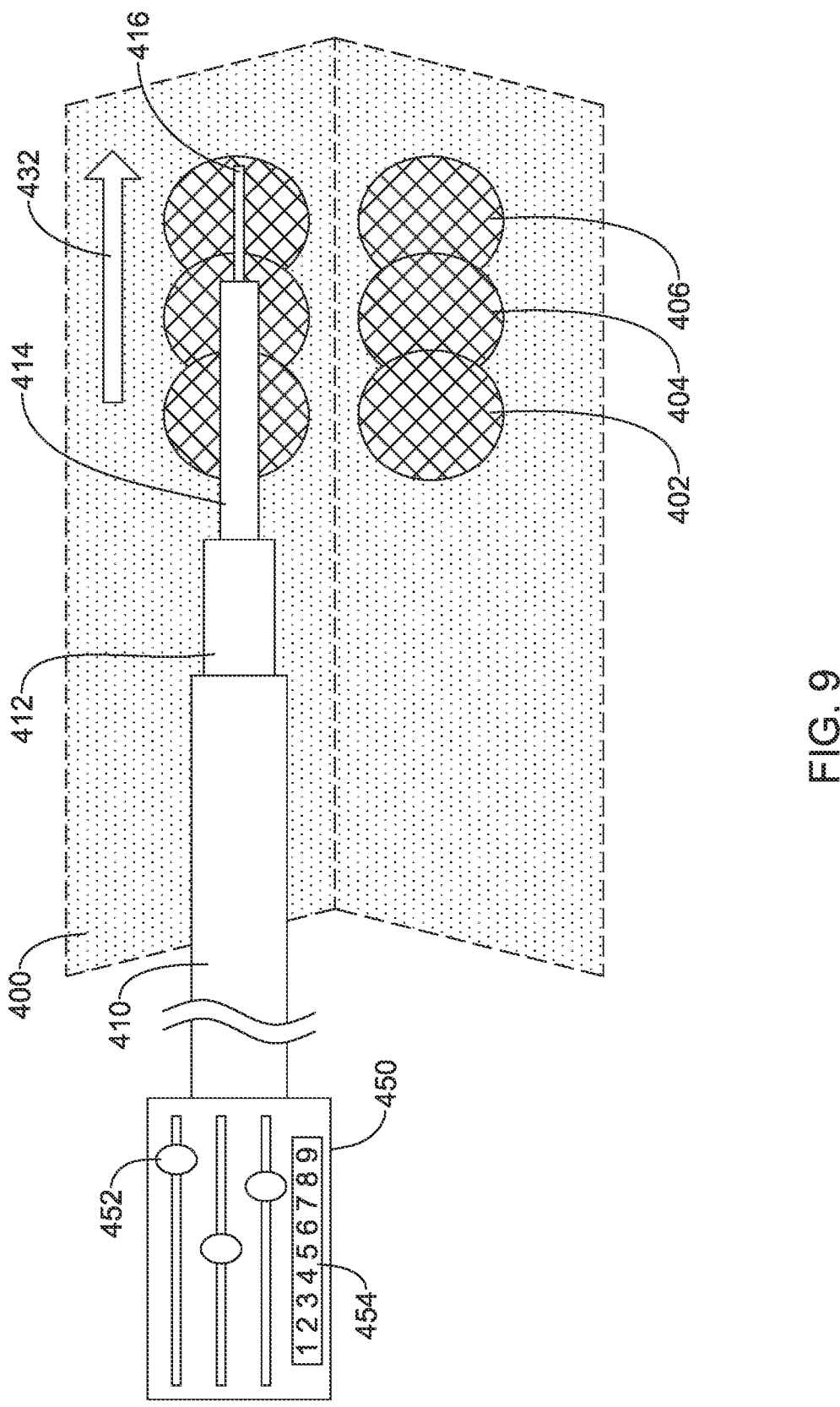

FIGS. 8-9 show additional ablation procedure steps with additional detail on the proximal end of an ablation probe. Staring with FIG. 8, a procedure is illustrated in which the probe, or at least the needle electrode 416, is withdrawn in stages. Here, the ablation probe is illustrated with an outer sheath 410, a shaft electrode 412, an inner sheath 414, and a needle electrode at 416. The proximal end of the ablation probe is shown having several mechanical stops available for manual activation. A first stop 420 can be used to fix the relative position of the outer sheath 410 and the shaft electrode, a second stop 422 can be used to fix the relative position of the shaft electrode and the inner sheath 414, and a third stop can be used to fix the relative position of the inner sheath 414 to the needle 416. Such fixation can be used in any of the procedures disclosed here.

One particular use of the fixation is illustrated in FIG. 8. Here, as indicated by arrow 430, a portion of the ablation probe is to be withdrawn in stages. A first lesion 406 is formed in a first ablation step. Prior to the first ablation step, the ablation probe is manipulated so that the surface area of the shaft electrode 412 is greater than the surface area of the needle electrode 416. The resulting lesion 406 is located at the needle electrode 416. Stoppers 420 and 424 are activated by the physician to fix the exposed surface areas of the shaft electrode 412 and needle electrode 416, respectively. Stopper 422 need not be activated here. After the first lesion 406 is formed, the combination of the needle electrode 416 and inner sheath 414 are withdrawn a desired distance, while the outer sheath 410 and shaft electrode 412 remain in position. A second ablation output is generated, yielding a second lesion 404. The process is repeated, and a third lesion is formed at 402. More lesions may be formed, as desired.

The signal generator 440 may be configured to adjust one or more parameters of the output energy, such as by reducing pulse width, pulse repetition rate, amplitude, or therapy duration, as each successive lesion is formed. Such adjustment may optionally be included to account for the reduced distance between the needle electrode 416 and the shaft electrode 412 for each successive therapy. The process may be performed in the reverse order, if desired. Rather than a step-by-step process with distinct lesions, a user may instead continuously withdraw the needle electrode and inner sheath to yield one elongated lesion. As shown in the illustration, the signal generator 440 may be coupled electrically to the electrodes 412, 416. Also, in the illustration, a temperature sensor is shown at 418, positioned between the electrodes 412, 416. In other examples, the temperature sensor 418 may be internal to the ablation probe and/or coupled to one or the other of the electrodes 412, 416; two or more temperature sensors may be provided if desired.

As noted, the signal generator 440 may be configured to maintain a selected temperature in the therapy region, such as by using a temperature sensor placed between the two therapy issuing electrodes (in a bipolar mode), or by using a temperature sensor placed near the active electrode (rather than the indifferent electrode for a monopolar mode). The signal generator can then adjust the therapy output to maintain a constant current at a target current level, while using the temperature sensor output to modify the target current level up or down to hold the target temperature.

The signal generator 440 may also be configured to obtain data from the ablation probe indicating how much surface area of each electrode is exposed, as well as how far apart the electrodes are. In so doing, the signal generator can adjust its interpretation of impedance data. For example, when more of the electrode surface area is exposed, the impedance would be expected to drop, as the electrode-tissue interface is larger, as well as the reverse. Further, when the electrodes are farther apart, the impedance would be expected to increase. If, for example, the signal generator observes a change in the current issued while the voltage is kept constant, the signal generator can thus distinguish between a change in tissue impedance due to tissue being ablated, from a change in impedance due to manipulation of electrode position. When the tissue impedance changes (such as by dropping) without a change in electrode size or position, the signal generator may treat this as indicating progress of the therapy. On the other hand, when the tissue impedance changes along with a change in electrode size or position, the signal generator may treat this as not indicating progress of the therapy, assuming the change in impedance is consistent with the change in electrode size or position.

As a further explanation, the ablation probe may include therein one or more potentiometers or other structures that change in (resistive) impedance under physical manipulation. In another example, parallel plates separated by a dielectric can be provided within the ablation probe and, as the plates are moved due to manipulation of the electrode size or distance, the capacitance of the parallel plates will change, allowing the signal generator to detect changing electrode configuration. Thus for example a plate may be disposed near the proximal end of the inner or outer shafts and/or the needle for such use.

In another example, all of the locking mechanisms can be enabled, and the entire ablation probe may be moved between successive ablation therapy outputs. In still another example, all of the locking mechanisms may be enabled and the entire ablation probe removed in a continuous fashion, as a way of ablating during removal to prevent tract seeding. Tract seeding can arise if malignant, but still viable, cells attach to the ablation probe and then fall off the ablation probe in the tract as the ablation probe is removed, effectively turning the therapy apparatus into a tumor spreader. Studies of rates of tract seeding with existing probes have estimated occurrence in 1% or more of cases, and so steps and apparatuses that can prevent tract seeding are of interest.

The locking mechanisms 420, 422, 424 may include, for example, a threaded screw that clamps down on the elements to be secured together, or which clamps down on attachments at/near the proximal end of the elements to be secured. Visual indicators may be provided to allow the user/surgeon to determine the relative spacings at the distal end of the ablation probe, as desired. For example, numbered indicia may be provided to indicate the surface area that is exposed at a given position.

FIG. 9 shows another example. Here, the ablation probe again has an outer sheath 410, shaft electrode 412, inner sheath 414, and needle electrode 416. A proximal manifold 450 is included in this example, and may include sliders 452 for example for controlling the relative position of the different pieces of the catheter at the distal end. Visual indicia 454 may be provided on the manifold 450. The indicia may indicate actual position, or may show the relative surface area exposure (at least for the electrodes 412, 416). In other examples, an automated or robotic control may be present in the manifold 450. In some examples, the manifold 450 may include a sensor or sensors to calculate the relative positions of the electrodes and their respective surface areas, and communicates such data to an associated signal generator. The signal generator can then calibrate output power to account for the available surface area and impedance. For example, a signal generator, having data regarding exposed surface area and impedance, and/or the distance between the electrodes, can prevent current flow from exceeding a defined upper limit to limit uncontrolled spread, arcing, or the like.

In use, as shown, a plurality of lesions can be formed as the needle electrode 416 is advanced from the ablation probe as shown by arrow 432. The needle electrode 416 may be advanced by itself or in combination with one or more of the inner sheath 414, the shaft electrode 412, and/or the outer sheath 410, as desired. In some examples, the needle electrode 416 and inner sheath 414 are locked together for advancing, in order to fix or hold constant the area of needle electrode 416 that is exposed. In some examples, the entire apparatus may be advanced as one, so that the exposed area of the electrodes 412, 416 remains fixed, as does the spacing between the two electrodes. In other examples, the surface area of each electrode may be kept fixed, but the spacing therebetween can change, and the signal generator may adjust its output, such as by increasing one or more of power, amplitude (voltage or current), pulse width, or pulse repetition rate as the spacing increases, or by decreasing one or more of power (voltage or current), amplitude, pulse width or pulse repetition rate as the spacing decreases. Such increase/decrease may be linear with respect to distance between the electrodes, or it may follow a more complex pattern, such as increasing with the square of the distance. For example, to maintain constant current as distance increases, the voltage would increase or decrease in direct proportion to the distance, while to maintain constant power, the voltage would increase or decrease in proportion to the square of the distance.

Figure 11:
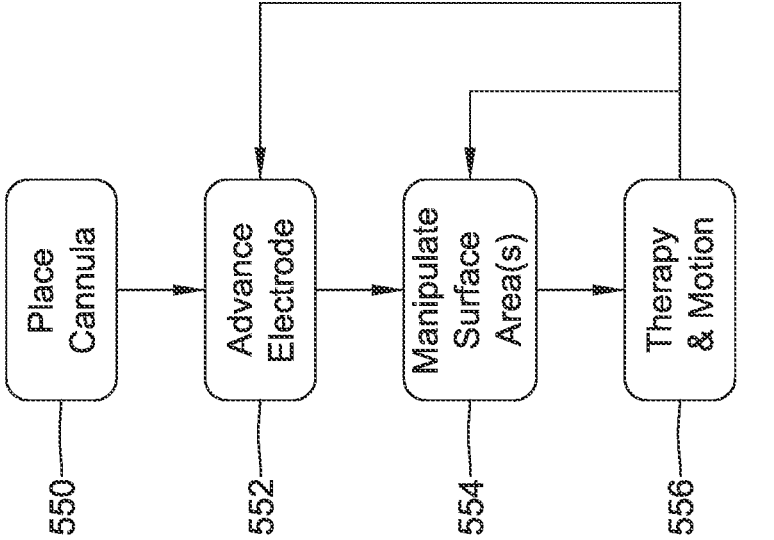
FIGS. 10-11 are process flow diagrams in block form for illustrative ablation procedures.
Figure 10:
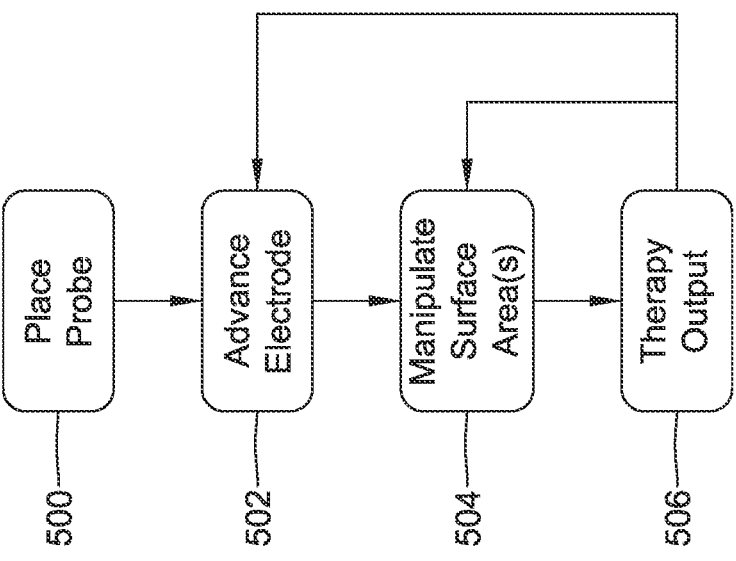

FIGS. 10-11 are process flow diagrams in block form for illustrative ablation procedures. FIG. 10 shows one illustrative method. Here, the probe is placed at a desired position in step 500, which may include advancing an ablation probe over or with the assistance of a guidewire, through an incision toward target tissue. Advancement may proceed through a body lumen in some examples (such as in a blood vessel, a mammary or other duct, a segment of the biliary tree, a portion of the alimentary canal, the esophagus or trachea, a renal duct, the urethra, or other passageways, etc.), while in other examples the probe is advanced through tissue without the use of any such body lumen or anatomical passageway. With the ablation probe positioned, one or more electrodes can be advanced to the target tissue in step 502. The surface area of one or more electrode surfaces is manipulated as indicated at 504; though block 504 is shown after step 502, the two may be swapped if desired. Therapy is then output as indicated at 506. The procedure may loop back to step 502 and/or to step 504, as desired, with movement of one or more electrodes and/or with manipulation of the surface area of one or more electrodes, as indicated. For example, a lesion as in FIG. 5 may be formed first, and then a lesion as in FIG. 6 or FIG. 7 may be performed, or any other suitable order.

FIG. 11 shows another example. Here, the ablation probe is again placed at 550, with or without the use of a body lumen or anatomical passageway. The electrode or electrodes are advanced, as indicated at 552. One or more surface areas of the electrodes are manipulated at 554 to achieve a desired relative surface area exposure. Then therapy is delivered as indicated at 556. In the example of FIG. 11, while therapy is issued, one or more of the electrodes used to output therapy is moved as well. This may include advancing or retracting the needle electrode, the shaft electrode, or both, as desired. Again, the procedure may loop back to blocks 552 and/or 554 for further ablation steps.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments. These embodiments are also referred to herein as "examples." Such examples can include elements in addition to those shown. The present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, innovative subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the protection should be determined with reference to the appended claims, along with the full scope of equivalents to which such claims are entitled.

What is claimed is:

1. A method of ablating a tissue region using a therapy probe having a shaft with proximal and distal ends, and a plurality of therapy delivery electrodes at the distal end thereof, the method comprising:

inserting the therapy probe to place the distal end of the shaft at a desired location, the distal end of the shaft including a shaft electrode having an exposed portion proximal of the distal end of the shaft, a surface area of the exposed portion of the shaft electrode being adjustable;

advancing a needle electrode from the shaft to a desired position and manipulating a needle electrode sheath that adjustably exposes a portion of the needle electrode to thereby control a surface area of the exposed portion of the needle electrode;

delivering a first therapy while a surface area of the exposed portion of the needle electrode exceeds a surface area of the exposed portion of the shaft electrode, to thereby develop a first lesion adjacent the shaft electrode; and delivering a second therapy while a surface area of the exposed portion of the shaft electrode exceeds the surface area of the exposed portion of the needle electrode, to thereby develop a second lesion adjacent the needle electrode.

2. The method of claim 1 further comprising manipulating the exposed portion of the needle electrode between the steps of delivering the first therapy and delivering the second therapy.

3. The method of claim 1 further comprising manipulating the exposed portion of the shaft electrode between the steps of delivering the first therapy and delivering the second therapy.

4. The method of claim 1 wherein the therapy probe is configured such that the position of the exposed portion of the shaft electrode is adjustable relative to the distal end of the therapy probe, and the method further comprises adjusting the position of the exposed portion of the shaft electrode between the steps of delivering the first therapy and delivering the second therapy.

5. The method of claim 1 wherein the first therapy takes the form of a thermal RF ablation therapy, and the second therapy takes the form of a thermal RF ablation therapy.

6. The method of claim 1 wherein the therapy probe comprises:

an outer sheath of a non-conductive material;

the needle electrode sheath, also of a non-conductive material;

the shaft electrode disposed between the needle electrode sheath and the outer sheath;

the needle electrode disposed within the needle electrode sheath;

a first locking hub configured for selectively locking a relative position of the outer sheath to the shaft electrode;

a second locking hub configured for selectively locking a relative position of the shaft electrode to the needle electrode sheath; and a third locking hub configured for selectively locking a relative position of the needle electrode sheath to the needle electrode.

7. The method of claim 6 further comprising:

locking the first and third locking hubs before delivering the first therapy;

unlocking at least one of the first or third locking hubs after delivering the first therapy and manipulating the exposed surface area of at least one of the shaft electrode or the needle electrode;

relocking the at least one of the first or third locking hubs after manipulating the exposed surface area of the at least one of the shaft electrode or he needle electrode, before delivering the second therapy.

8. A method of ablating a tissue region using an ablation probe having a shaft with proximal and distal ends, and a plurality of therapy delivery electrodes at the distal end thereof, the method comprising:

inserting the ablation probe to place the distal end of the shaft at a desired location, the distal end of the shaft including a shaft electrode having an exposed portion proximal of the distal end of the shaft, a surface area of the exposed portion of the shaft electrode being adjustable;

advancing a needle electrode from the shaft to a desired position and manipulating a needle electrode sheath that adjustably exposes a portion of the needle electrode to thereby control a surface area of the exposed portion of the needle electrode;

delivering a first therapy while a surface area of the exposed portion of the shaft electrode exceeds the surface area of the exposed portion of the needle electrode, to thereby develop a first lesion adjacent the needle electrode and, during delivery of the first therapy, withdrawing the needle electrode from the desired position and into the shaft while maintaining the exposed surface area of the needle electrode, to thereby extend the first lesion in a longitudinal direction relative to an axis of the needle electrode.

9. The method of claim 8 wherein the therapy probe comprises:

an outer sheath of a non-conductive material;

the needle electrode sheath, also of a non-conductive material;

the shaft electrode disposed between the needle electrode sheath and the outer sheath;

the needle electrode disposed within the needle electrode sheath;

a first locking hub configured for selectively locking a relative position of the outer sheath to the shaft electrode;

a second locking hub configured for selectively locking a relative position of the shaft electrode to the needle electrode sheath; and a third locking hub configured for selectively locking a relative position of the needle electrode sheath to the needle electrode.

10. The method of claim 9 further comprising:

locking the first and third locking hubs before delivering the first therapy, to thereby fix the exposed surface areas of each of the shaft electrode and the needle electrode, while leaving the second locking hub unlocked to allow withdrawal of the needle electrode from the desired position and into the shaft.

11. The method of claim 8 further comprising reducing a power level of the first therapy as the needle electrode is withdrawn from the desired position and into the shaft.

12. The method of claim 8 further comprising sensing an impedance between the needle electrode and the shaft electrode, and sensing at least one temperature at a position adjacent the needle electrode, and responsive to the sensed impedance and at least one temperature, adjusting the power level of the first therapy as the needle electrode is withdrawn from the desired position and into the shaft.

13. A system for ablation, comprising:

an ablation probe having a proximal end and a distal end, the ablation probe comprising:

an outer sheath of a non-conductive material;

an inner sheath of a non-conductive material;

a shaft electrode disposed between the inner and outer sheaths;

a needle electrode disposed within the inner sheath;

a first locking hub configured for selectively locking a relative position of the outer sheath to the shaft electrode;

a second locking hub configured for selectively locking a relative position of the shaft electrode to the inner sheath;

a third locking hub configured for selectively locking a relative position of the inner sheath to the needle electrode; and means to indicate electrically a change in exposed surface area of at least one of the shaft and needle electrodes and/or means to indicate electrically a change in a distance between the shaft and needle electrodes; and a signal generator adapted for electrical connection to each of the needle electrode and the shaft electrode, the signal generator configured to sense the distance between the electrodes and the surface area of the electrodes by linking to the locking hubs.

14. The system for ablation of claim 13 wherein the needle electrode, inner sheath, shaft electrode, and outer sheath are each moveable relative to one another when none of the locking hubs are locked.

15. The system for ablation of claim 13 wherein the third locking hub facilitates a step of defining an exposed surface area of the needle electrode, and the first locking hub facilitates a step of defining an exposed surface area of the shaft electrode, such that, in use, a user may lock the first and third locking hubs while moving the needle electrode, having a fixed surface area, relative to the shaft electrode, also having a fixed surface area.

16. The system for ablation claim 15 wherein the signal generator is configured to sense an impedance between the needle electrode and the shaft electrode during therapy delivery to maintain a constant therapy current as the needle electrode and the shaft electrode are moved relative to one another.

17. The system for ablation of claim 13, further comprising a temperature sensor associated with at least one of the shaft electrode or the needle electrode.

18. The system for ablation of claim 17 wherein the signal generator is configured to sense an impedance between the needle electrode and the shaft electrode during therapy delivery and to obtain a temperature signal from the temperature sensor, and to adjust a therapy voltage responsive to the temperature and impedance signals.

19. The system for ablation of claim 18 wherein the signal generator is configured to operate as follows:

at initiation of a therapy output, sense temperature and impedance;

maintain or increase voltage until the sensed temperature reaches a temperature threshold;

measure impedance and voltage once the sensed temperature reaches the temperature threshold and store a target current;

after the temperature threshold is reached, monitor impedance to maintain the target current; and if the sensed temperature rises above the temperature threshold, reduce the target current.

20. The system for ablation of claim 13, wherein the outer sheath includes a manifold, and the means to indicate electrically the change in exposed surface area includes at least one sensor for calculating the relative positions of the shaft and needle electrodes and their respective surface areas.

* * * * *